(12) United States Patent
Lin et al.

(10) Patent No.: US 10,233,628 B2
(45) Date of Patent: Mar. 19, 2019

(54) ELECTROLYTIC WATER URINAL

(71) Applicant: JOMOO KITCHEN & BATH CO., LTD., Nan'an (CN)

(72) Inventors: Xiaofa Lin, Nan'an (CN); Xiaoshan Lin, Nan'an (CN); Libin Shen, Nan'an (CN); Sheng Ye, Nan'an (CN)

(73) Assignee: JOMOO KITCHEN & BATH CO., LTD., Nan'an (CN)

( * ) Notice: Subject to any disclaimer, the term of this patent is extended or adjusted under 35 U.S.C. 154(b) by 0 days.

(21) Appl. No.: 15/649,653

(22) Filed: Jul. 14, 2017

(65) Prior Publication Data

US 2018/0171617 A1 Jun. 21, 2018

(30) Foreign Application Priority Data

Dec. 16, 2016 (CN) .......................... 2016 1 1169159

(51) Int. Cl.
*E03D 13/00* (2006.01)
*A61L 2/18* (2006.01)
*C02F 1/461* (2006.01)
*E03D 9/00* (2006.01)
*A61L 2/22* (2006.01)

(52) U.S. Cl.
CPC .............. *E03D 13/005* (2013.01); *A61L 2/18* (2013.01); *A61L 2/22* (2013.01); *C02F 1/4618* (2013.01); *E03D 9/002* (2013.01); *E03D 9/005* (2013.01); *A61L 2202/11* (2013.01); *A61L 2202/14* (2013.01); *A61L 2202/17* (2013.01); *C02F 2201/46145* (2013.01); *C02F 2301/028* (2013.01); *C02F 2303/02* (2013.01); *C02F 2303/04* (2013.01); *C02F 2303/22* (2013.01)

(58) Field of Classification Search
CPC ....... E03D 13/00; E03D 13/005; A61L 2/035; C02F 1/4618
See application file for complete search history.

(56) References Cited

U.S. PATENT DOCUMENTS

| 2004/0133968 | A1* | 7/2004 | Hoehne | .................. | B64D 11/02 |
| | | | | | 4/233 |
| 2009/0148341 | A1* | 6/2009 | Kanno | ..................... | A61L 2/035 |
| | | | | | 422/29 |
| 2015/0275496 | A1* | 10/2015 | Yaoka | ..................... | E03D 13/00 |
| | | | | | 4/310 |

FOREIGN PATENT DOCUMENTS

CN 202023244 U 11/2011

* cited by examiner

*Primary Examiner* — Janie M Loeppke
(74) *Attorney, Agent, or Firm* — Gokalp Bayramoglu

(57) ABSTRACT

The present invention discloses an electrolytic water urinal. The electrolytic water urinal includes an electrolysis module and a urinal body. The electrolysis module produces the acidic electrolytic water and the alkaline electrolytic water. The electrolysis module includes a first water outlet and a second water outlet. The urinal body includes a bowl water inlet which is provided on an upper portion of the urinal body. The first water outlet and the second water outlet of the electrolysis module are connected to the bowl water inlet of the urinal body. The acidic electrolytic water and the alkaline electrolytic water produced by the electrolysis module are sprayed on an inner wall of the urinal body alternately or simultaneously through the bowl water inlet so as to perform washing from top to bottom.

12 Claims, 12 Drawing Sheets

ELECTROLYTIC WATER URINAL

CROSS REFERENCE

This application claims priority to Chinese Patent Application No. 201611169159.1, filed on Dec. 16, 2016, the entire contents of which are incorporated herein by reference.

TECHNICAL FIELD

The present invention relates to the urinal, particularly to an electrolytic water urinal.

BACKGROUND

Existing urinals usually use neutral water, such as tap water and so on, to perform cleaning by washing the wall surface of the urinal body. However, since the major ingredients of the urine scales on the urinal body are calcium carbonate, magnesium carbonate, calcium sulfate, magnesium sulfate, etc., using neutral water such as the tap water, to clean the urinal usually does not achieve the functions of sterilization, disinfection, deodorization, and urine scale removal, etc. Thus, it is necessary to fully clean the urinal with detergent manually and regularly. This not only increases the labor cost of the cleaning work, but also makes it hard to meet the requirements of people to improve the quality of life and environment.

For example, a Chinese utility model patent with application No. CN201120124087.5 provides a toilet with a function of electrolyte spray disinfection, which includes a tank and a sealed housing provided next to the tank. The housing is provided with an electric water valve, an electrolytic cell connected to the electric water valve through a pipe, an atomizing nozzle connected to the electrolytic cell through a pipe, a driving circuit impelling the tap water to flow through the electrolytic cell and to be sprayed through the atomizing nozzle, a power supply connected to the driving circuit, and a high pressure generator provided on the water inlet pipe of the atomizing nozzle. The atomizing nozzle extends to where the water is sprayed in the sanitary facility tank. A power switch and function keys are provided on the top of the sealed housing.

Though the toilet uses the electrolytic cell to electrolyze the tap water to wash the toilet, at the water outlet of the toilet, the mixed mist spray of acidic water and the alkaline water produced by the electrolytic cell makes the acidic water and the alkaline water contact each other, which leads to a neutralization reaction, and thereby losing the functions of sterilization and disinfection.

SUMMARY

The purpose of the present invention is to solve the problems in the prior art and provide a urinal which uses electrolytic water to clean the urinal.

In order to achieve the above purpose, the present invention provides the following technical solutions. An electrolytic water urinal includes an electrolysis module producing acidic electrolytic water and alkaline electrolytic water and including a first water outlet and a second water outlet, and a urinal body including a bowl water inlet provided on an upper portion of the urinal body; wherein the first water outlet and the second water outlet of the electrolysis module are configured to alternately discharge the acidic electrolytic water and the alkaline electrolytic water and separately connected to the bowl water inlet of the urinal body. The acidic electrolytic water and the alkaline electrolytic water produced by the electrolysis module are alternately or separately spreyed on an inner wall of the urinal body through the bowl water inlet to perform washing from top to bottom.

Preferably, the present invention further includes a water storage module including a first reservoir and a second reservoir isolated from each other, a first control valve, a second control valve, and a tube; wherein a water inlet of the first reservoir is connected to the first water outlet of the electrolysis module through the tube; a water outlet of the first reservoir, the first control valve, and the bowl water inlet of the urinal body are connected in turn through the tube; a water inlet of the second reservoir is connected to the second water outlet of the electrolysis module through the tube; a water outlet of the second reservoir, the second control valve, and the bowl water inlet of the urinal body are connected in turn through the tube; and the acidic electrolytic water and the alkaline electrolytic water are alternately sprayed on the inner wall of the urinal body through the bowl water inlet so as to perform washing from top to bottom. Preferably, the acidic electrolytic water washes the inner wall of the urinal body from top to bottom first, and the alkaline electrolytic water starts to wash the inner wall of the urinal body from top to bottom subsequently; or the alkaline electrolytic water washes the inner wall of the urinal body from top to bottom first, and the acidic electrolytic water starts to wash the inner wall of the urinal body from top to bottom subsequently.

Preferably, the present invention further includes a first water storage module, a second water storage module, a first control valve, a second control valve, and a tube; wherein a water inlet of the first water storage module is connected to the first water outlet of the electrolysis module through the tube; a first water outlet of the first water storage module, the first control valve, and the bowl water inlet of the urinal body are connected in turn through the tube; a water inlet of the second water storage module is connected to the second water outlet of the electrolysis module through the tube; a second water outlet of the second water storage module, the second control valve, and the bowl water inlet of the urinal body are connected in turn through the tube. The acidic electrolytic water and the alkaline electrolytic water are alternately sprayed on the inner wall of the urinal body through the bowl water inlet.

Preferably, each of the first water storage module and the second water storage module includes a reservoir body provided with a water inlet and a water outlet, a spring, and a push plate; the spring and the push plate are both provided in the reservoir body; the spring is fixed between the push plate and an inner wall of the reservoir body and is provided far away from the water inlet of the reservoir body and the water outlet of the reservoir body; when water is filled into the second water storage module or the first water storage module, the alkaline electrolytic water or the acidic electrolytic water enters the reservoir body and pushes the push plate to compress the spring so as to achieve a water storage; and when the water is discharged from the second water storage module or the first water storage module, a compressed spring pushes the push plate to move, such that the alkaline electrolytic water or the acidic electrolytic water in the reservoir body is discharged by means of the push plate under a pressure so as to achieve water discharging.

Preferably, the present invention further includes a water storage module including a water inlet and a water outlet that are both provided on top of the water storage module, a control valve, and a tube; wherein the water inlet of the water storage module is connected to the second water outlet of the electrolysis module through the tube; the water outlet of the water storage module and the first water outlet of the electrolysis module are connected to each other and jointly connected to the control valve and the bowl water inlet of the urinal body in turn through the tube.

Preferably, the water storage module is provided with at least one baffle plate; and the baffle plate separates a water storage space in the water storage module into a plurality of serpentine channels that are connected to each other.

Preferably, when the acidic electrolytic water or the alkaline electrolytic water enters the water storage module, the acidic electrolytic water or the alkaline electrolytic water horizontally enters the water inlet of the water storage module, and gradually flows to the water outlet of the water storage module from bottom to top through the plurality of serpentine channels provided horizontally, so as to evacuate air in the serpentine channels of the water storage module.

Preferably, the acidic electrolytic water directly washes the inner wall of the urinal body from top to bottom and the alkaline electrolytic water is stored in the water storage module; when a certain amount of the alkaline electrolytic water is stored, the electrolysis module stops an electrolysis operation, and neutral cleaning water is introduced through the water inlet of the water storage module; the neutral cleaning water enters the water storage module to force the alkaline electrolytic water in the water storage module to enter the urinal body, so as to wash the inner wall of the urinal body from top to bottom; and after discharging of the alkaline electrolytic water is finished, the neutral cleaning water enters the urinal body, so as to wash the inner wall of the urinal body from top to bottom; or the alkaline electrolytic water directly washes the inner wall of the urinal body from top to bottom and the acidic electrolytic water is stored in the water storage module; when a certain amount of the acidic electrolytic water is stored, the electrolysis module stops an electrolysis operation, and neutral cleaning water is introduced through the water inlet of the water storage module; the neutral cleaning water enters the water storage module to force the acidic electrolytic water in the water storage module to enter the urinal body, so as to wash the inner wall of the urinal body from top to bottom; and after discharging of the acidic electrolytic water is finished, the neutral cleaning water enters the urinal body, so as to wash the inner wall of the urinal body from top to bottom.

Preferably, the present invention further includes an electrolytic water control module controlling the electrolysis module to switch electrodes, and a nozzle provided at the bowl water inlet of the urinal body and including a first spout, a second spout, and a baffle plate provided between the first spout and the second spout; wherein the first spout and the second spout are provided adjacently and are spaced by the baffle plate; the first spout is connected to the first water outlet of the electrolysis module directly; and the second spout is connected to the second water outlet of the electrolysis module directly.

Preferably, the acidic electrolytic water and the alkaline electrolytic water are sprayed simultaneously on inner walls of both sides of the urinal body from the first spout and the second spout of the nozzle respectively Preferably, the present invention further includes an electrolytic water control module controlling the electrolysis module to switch electrodes; wherein after the electrodes of the electrolysis module is switched through the electrolytic water control module, in the electrolysis module, the first water outlet is configured to discharge the alkaline electrolytic water, and the second water outlet is configured to discharge the acidic electrolytic water.

Preferably, before performing an electrolysis through the electrolysis module to produce the acidic electrolytic water and the alkaline electrolytic water, water is required to be supplied in the electrolysis module first, and a power is then supplied to start the electrolysis module.

Compared to the prior art, the advantages of the technical solutions of the present invention include:

1. In the electrolytic water urinal, the acidic electrolytic water and the alkaline electrolytic water produced by the electrolysis module are used to separately wash the urinal body, and converge at the bottom of the urinal body to lead to a neutralization reaction for producing neutral water. In the washing process, the acidic electrolytic water may directly and chemically react with the urine scale. Further, the functions of sterilization and disinfection of the acidic electrolytic water are maintained. Thus, the functions of sterilization, disinfection, deodorization, and urine scale removal from the electrolytic water urinal can be improved.

2. In the electrolytic water urinal, the acidic electrolytic water and the alkaline electrolytic water are used to wash the urinal body alternately. The neutralization reaction occurs at the bottom of the urinal body to produce neutral water. Thus, the following problem is avoided, i.e., when the acidic electrolytic water and the alkaline electrolytic water are discharged at the same time, they contact each other, which leads to the neutralization reaction and thereby losing the functions of sterilization and disinfection. Thus, the functions of sterilization, disinfection, deodorization, and urine scale removal from the electrolytic water urinal are improved.

3. In the electrolytic water urinal, each of the second water storage module and the first water storage module is provided with a spring. The functions of energy storage and water storage are achieved through the extension and retraction of the spring. Moreover, the acidic electrolytic water and the alkaline electrolytic water can be discharged under a pressure, such that a jet washing flow with a certain flow velocity is sprayed on the inner wall of the urinal body. Not only it provides a better washing effect, but also saves water. Moreover, since the acidic electrolytic water and the alkaline electrolytic water alternately wash the urinal body, the following problem can be avoided, i.e., when the acidic electrolytic water and the alkaline electrolytic water are discharged at the same time, they contact each other, which leads to the neutralization reaction, and thereby losing the functions of sterilization and disinfection. Thus, the functions of sterilization, disinfection, deodorization, and urine scale removal from the electrolytic water urinal are improved.

4. In the electrolytic water urinal, the first spout and the second spout of the nozzle are used to make the acidic electrolytic water and the alkaline electrolytic water respectively wash the inner walls of both sides of the urinal body. Moreover, the problem that the acidic electrolytic water and the alkaline electrolytic water contact each other, which leads to the neutralization reaction, and thereby losing the function of sterilization and disinfection is avoided. Thus, the functions of sterilization, disinfection, deodorization, and urine scale removal from the electrolytic water urinal are improved. Also, the electrolytic water controlling module controls the electrolysis module to switch the cathode and the anode, such that the washing operations in which the acidic electrolytic water and the alkaline electrolytic water are exchanged are achieved. Not only can lifetimes of electrodes of the electrolytic cell be improved, but also the urinal can be washed better.

5. In the electrolytic water urinal, the washing process of the electrolytic water urinal includes an acidic washing step, an alkaline washing step, and a neutral water washing step. These steps are performed separately and sequentially. Thus, the acidic electrolytic water and the alkaline electrolytic water alternately wash the urinal body. Also, at the bottom of the urinal body, the neutralization reaction occurs to produce neutral water. Thus, the following problem can be avoided, i.e., when the acidic electrolytic water and the alkaline electrolytic water are output at the same time, they contact each other, which leads to the neutralization reaction, and thereby losing the functions of sterilization and disinfection. Thus, the functions of sterilization, disinfection, deodorization, and urine scale removal from the electrolytic water urinal are improved.

BRIEF DESCRIPTION OF THE DRAWINGS

Drawings described herein are used to provide further understanding of the present invention and constitute a part of the present invention. Exemplary embodiments of the present invention and descriptions thereof are used to interpret the present invention, but are not intended to limit the present invention. In the drawings.

DETAILED DESCRIPTION

To make the technical problems to be solved, the technical solutions, and the advantages of the present invention more explicit and clear, hereinafter, the present invention is described in detail with reference to the drawings and embodiments. Specific embodiments described herein are merely used to interpret the present invention, but are not used to limit the present invention.

Embodiment 1

Figure 1:
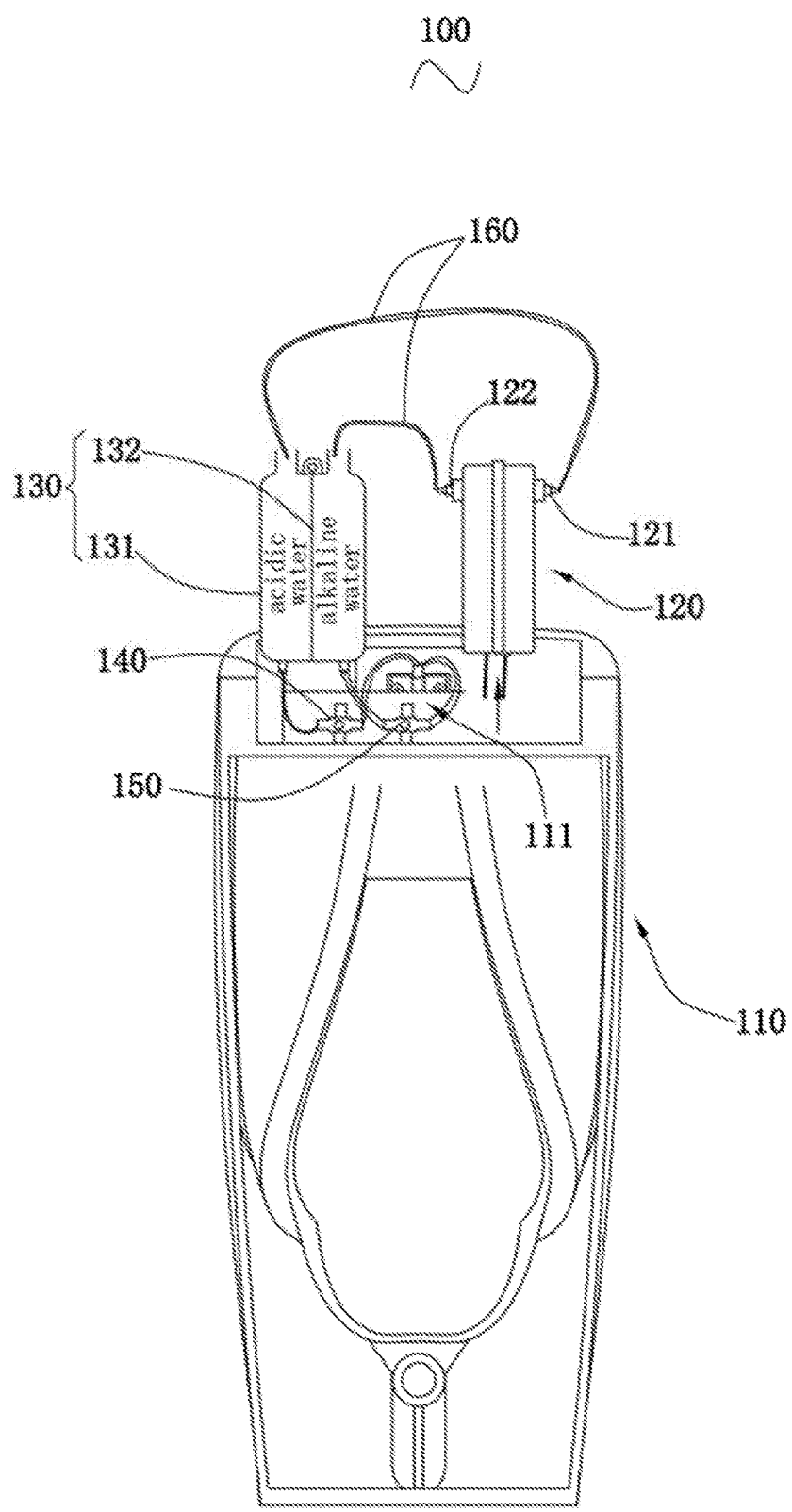
FIG. 1 is the structural schematic diagram of the electrolytic water urinal provided by Embodiment 1 of the present invention.
Figure 2:
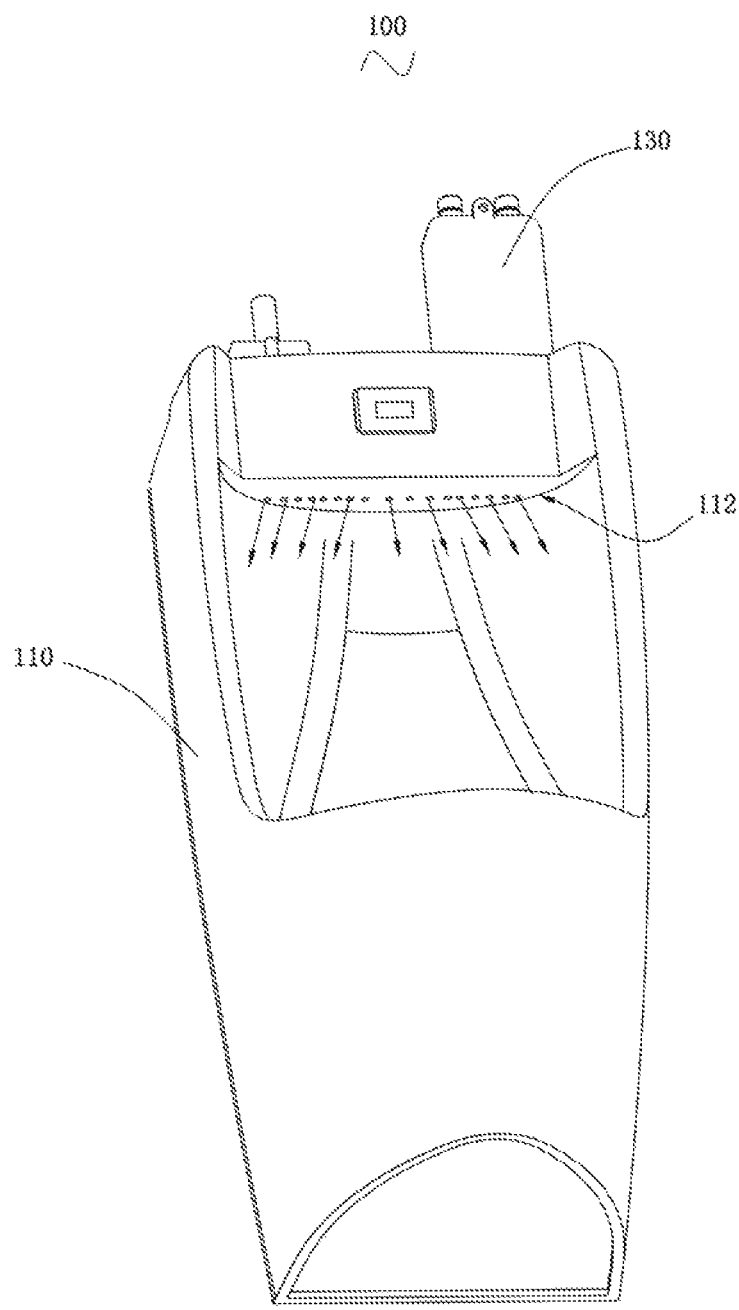
FIG. 2 is the assembling structural schematic diagram of the electrolytic water urinal as shown in FIG. 1.

Referring to both FIG. 1 and FIG. 2, FIG. 1 is the structural schematic diagram of the electrolytic water urinal provided by this embodiment of the present invention. FIG. 2 is the assembling structural schematic diagram of the electrolytic water urinal as shown in FIG. 1. The electrolytic water urinal 100 includes a urinal body 110, an electrolysis module 120, a water storage module 130, a first control valve 140, a second control valve 150, and tubes 160. Preferably, the first control valve 140 and the second control valve 150 are solenoid valves. Optionally, tubes 160 may be plastic tubes or tubes made of metal, to which the present invention is not limited.

The urinal body 110 includes a bowl water inlet 111, which is provided on the upper portion of the urinal body. Further, the urinal body 110 is also provided with a plurality of drain holes 112, which are connected to the bowl water inlet 111. A plurality of drain holes 112 are distributed evenly and uniformly on the inner side of the top of the urinal body 110.

The electrolysis module 120 produces acidic electrolytic water and alkaline electrolytic water, and includes a first water outlet 121 which is configured to discharge the acidic electrolytic water and a second water outlet 122 which is configured to discharge the alkaline electrolytic water.

The water storage module 130, which is a reservoir, is provided on the top of the urinal body 110. The water storage module 130 includes a first reservoir 131 and a second reservoir 132 that are isolated from each other. The water inlet of the first reservoir 131 is connected to the first water outlet 121 of the electrolysis module 120 through the tube 160. The water outlet of the first reservoir 131, the first control valve 140, and the bowl water inlet 111 of the urinal body 110 are connected in turn through the tube 160.

The water inlet of the second reservoir 132 is connected to a second water outlet 122 of the electrolysis module 120 through the tube 160. The water outlet of the second reservoir 132, the second control valve 150, and the bowl water inlet 111 of the urinal body 110 are connected in turn through the tube 160.

In the present embodiment, the electrolysis module 120 can produce the equal amounts of the acidic electrolytic water and the alkaline electrolytic water. The acidic electrolytic water and the alkaline electrolytic water are respectively stored in the first reservoir 131 and the second reservoir 132 of the water storage module 130.

Moreover, the first water outlet 121 and the second water outlet 122 of the electrolysis module 120 are connected to the bowl water inlet 111 of the urinal body 110 through the water storage module 130, such that the acidic electrolytic water and the alkaline electrolytic water eventually flow into the urinal body 110.

When the user is using the electrolytic water urinal 100, normally, the electrolysis module 120 of the electrolytic water urinal 100 does not start. Regular tap water is used to wash the electrolytic water urinal 100 to perform the neutral water washing.

When there is no user using the electrolytic water urinal 100, the electrolytic water urinal 100 would automatically start the electrolysis module 120 to produce the acidic electrolytic water and the alkaline electrolytic water to perform electrolytic water washing on the electrolytic water urinal 100. Further, the electrolytic water urinal 100 selects a predetermined time interval to perform electrolytic water washing operation once. For example, the electrolytic water urinal 100 may perform electrolytic water washing operation every 6 hours, 12 hours, 24 hours, etc.

Moreover, before performing the electrolysis through the electrolysis module 120 to produce the acidic electrolytic water and the alkaline electrolytic water, it is required that the water is first supplied in the electrolysis module 120, and next the power is supplied to start the electrolysis module 120.

The electrolytic water washing process of the electrolytic water urinal 100 includes an acidic washing step and an alkaline washing step that are performed separately.

In the acidic washing step, the electrolytic water urinal 100 starts to work, and the first control valve 140 is open, such that the acidic electrolytic water enters the bowl water inlet 111 of the urinal body 110 from the first reservoir 131 of the water storage module 130, and is sprayed evenly on the inner wall of the urinal body 110 through a plurality of drain holes 112, so as to implement the acidic washing operation from top to bottom. During this time, the alkaline electrolytic water remains stored in the second reservoir 132 of the water storage module 130.

After finishing the acidic electrolytic water washing, the alkaline washing step is then performed. The first control valve 140 is closed, and the second control valve 150 is open, such that the alkaline electrolytic water enters the bowl water inlet 111 of the urinal body 110 from the second reservoir 132 of the water storage module 130, and is sprayed evenly on the inner wall of the urinal body 110 through a plurality of drain holes 112, so as to implement the alkaline washing operation from top to bottom. Thus, the electrolytic water washing process of the urinal body 110 is performed once.

That is, the acidic electrolytic water and the alkaline electrolytic water produced by the electrolysis module 120 are separate from each other and are sprayed on the inner wall of the urinal body 110 alternately through the water inlet 111 of the bowl urinal body 110, so as to fulfill the washing operation of the electrolytic water urinal 100.

In other alternative embodiments, in the washing process of the electrolytic water urinal 100, the alkaline washing step may be performed first and the acidic washing step may be performed subsequently. The specific process is similar to the electrolytic water washing process as described above, and thus the details are omitted here.

Optionally, the electrolytic water urinal 100 may also include an electrolytic water controlling module (not shown) which controls the electrolysis module 120 to switch the electrodes. The electrolytic water controlling module may be hardware, such as a control circuit, a control chip, a programmable single chip, and so on, and may also be software, to which the present invention is not limited.

After the electrolytic water controlling module controls the electrolysis module 120 to switch the electrodes, in the electrolysis module 120, the first water outlet 121 is configured to discharge the alkaline electrolytic water, and the second water outlet 122 is configured to discharge the acidic electrolytic water. Correspondingly, the first reservoir 131 of the water storage module 130 is configured to store alkaline electrolytic water discharged by the first water outlet 121, and the second reservoir 132 is configured to store acidic electrolytic water discharged by the second water outlet 122.

Embodiment 2

Figure 3:
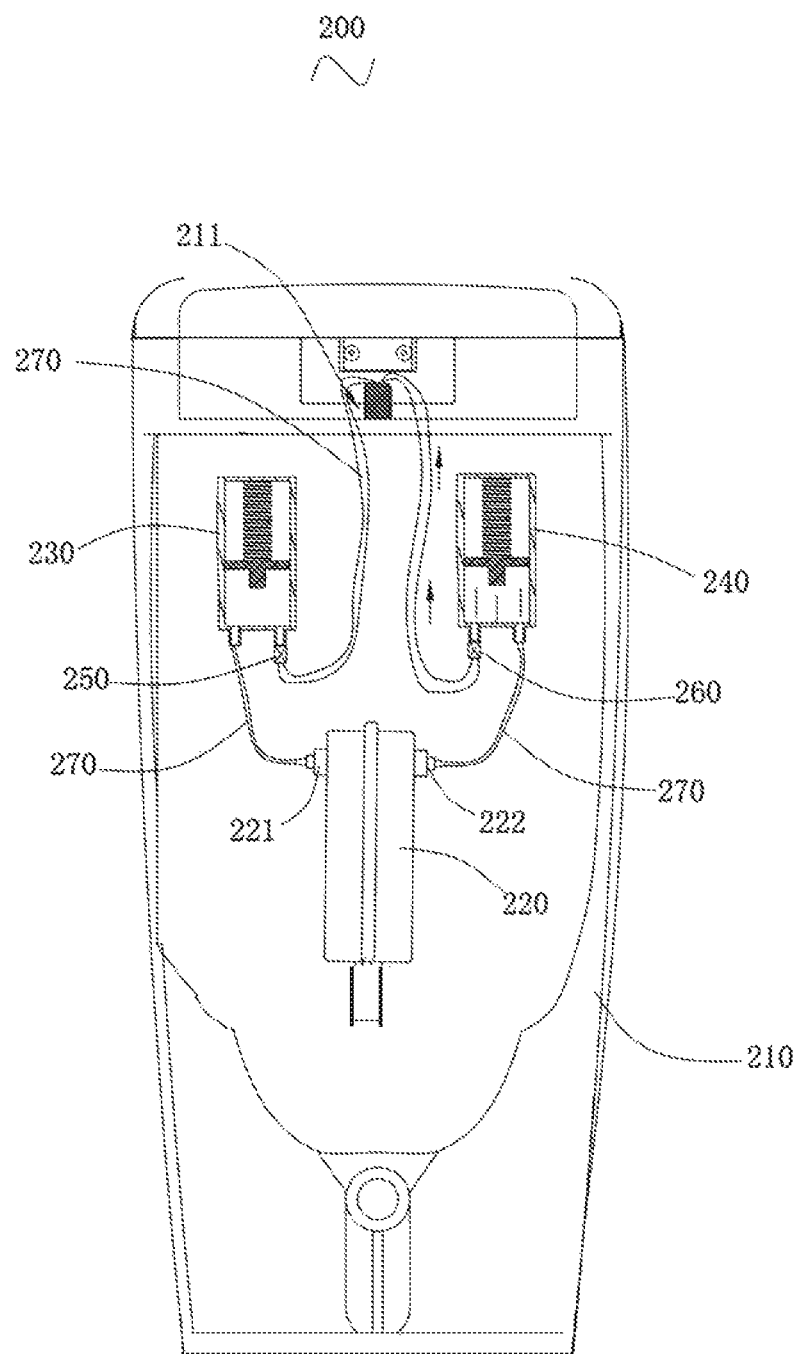
FIG. 3 is the structural schematic diagram of the electrolytic water urinal provided by Embodiment 2 of the present invention.
Figure 4:
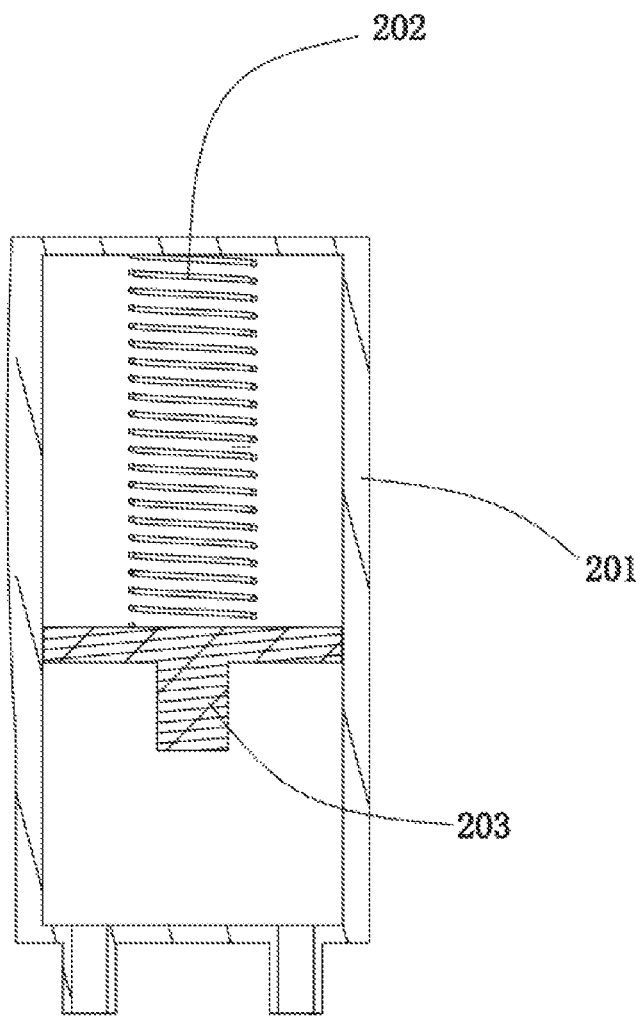
FIG. 4 is the structural schematic diagram of the water storage module in the electrolytic water urinal as shown in FIG. 3.

Referring to both FIG. 3 and FIG. 4, FIG. 3 is the structural schematic diagram of the electrolytic water urinal provided by Embodiment 2 of the present invention. FIG. 4 is the structural schematic diagram of the first water storage module and the second water storage module in the electrolytic water urinal as shown in FIG. 3. The electrolytic water urinal 200 includes a urinal body 210, an electrolysis module 220, a first water storage module 230, a second water storage module 240, a first control valve 250, a second control valve 260, and tubes 270. Preferably, the first control valve 250 and the second control valve 260 are solenoid valves. Optionally, tubes 270 may be plastic tubes or tubes made of metal, to which the present invention is not limited.

The urinal body 210 includes a bowl water inlet 211 which is provided on the upper portion of the urinal body. Further, the urinal body 210 may also be provided with a nozzle (not shown) which is connected to the bowl water inlet 211. The nozzle is provided on the inner side of the top of the urinal body 210 and the nozzle has an opening oriented to the inside of the urinal body 210.

The electrolysis module 220 produces the equal amounts of the acidic electrolytic water and the alkaline electrolytic water simultaneously and includes a first water outlet 221 configured to discharge the acidic electrolytic water and a second water outlet 222 configured to discharge the alkaline electrolytic water.

Both the first water storage module 230 and the second water storage module 240 are reservoirs and are configured to store the acidic electrolytic water and the alkaline electrolytic water respectively.

The water inlet of the first water storage module 230 is connected to the first water outlet 221 of the electrolysis module 220 through the tube 270. The water outlet of the first water storage module 230, the first control valve 250, and the bowl water inlet 211 of the urinal body 210 are connected in turn through the tube 270.

The water inlet of the second water storage module 240 is connected to the alkaline water outlet 222 of the electrolysis module 220 through the tube 270. The water outlet of the second water storage module 240, the second control valve 260, and the bowl water inlet 211 of the urinal body 210 are connected in turn through the tube 270.

In the present embodiment, both the first water storage module 230 and the second water storage module 240 include a reservoir body 201 provided with a water inlet and outlet, a spring 202, and a push plate 203. The spring 202 and the push plate 203 are both provided in the reservoir body 201. The spring 202 is fixed between the push plate 203 and an inner wall of the reservoir body 201 and is provided far away from the water inlet and outlet of the reservoir body 201.

Figure 5:
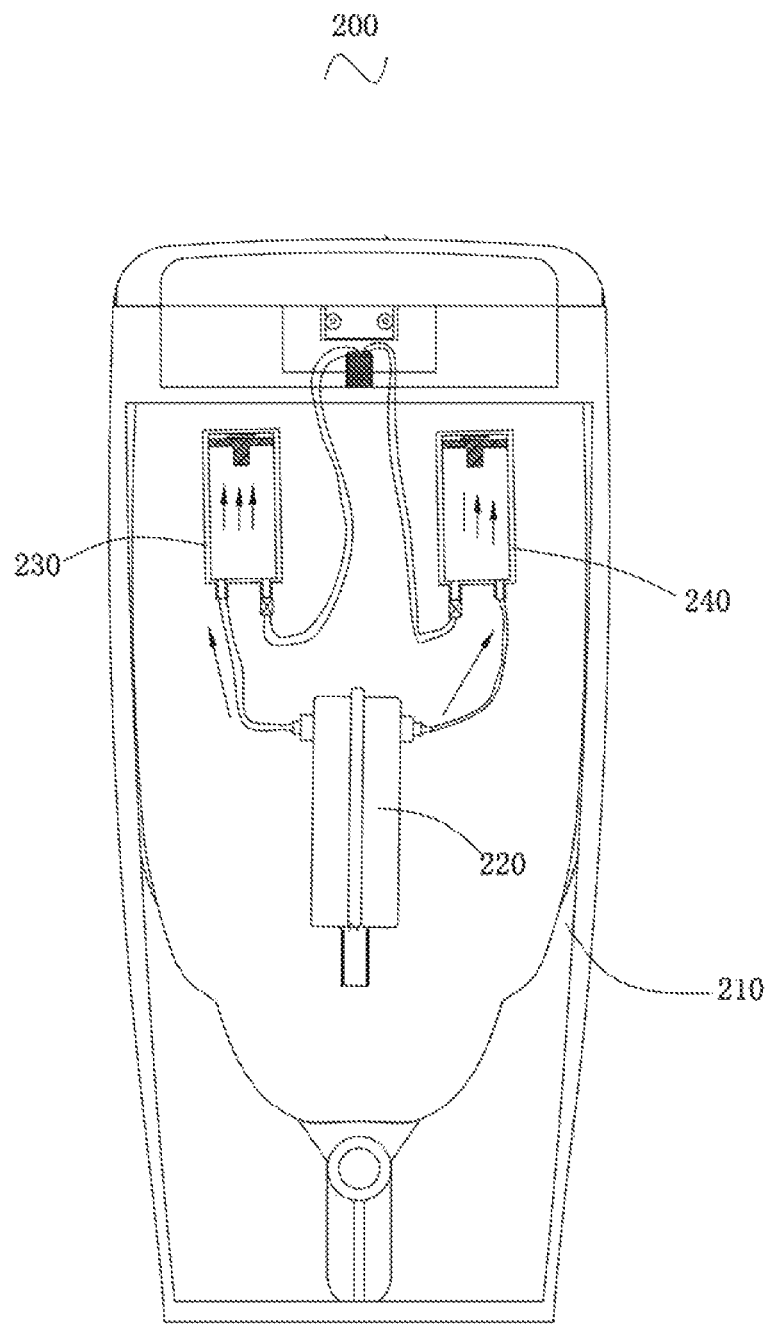
FIG. 5 is the schematic diagram of the water input of the second water storage module and the first water storage module in the electrolytic water urinal as shown in FIG. 3.
Figure 6:
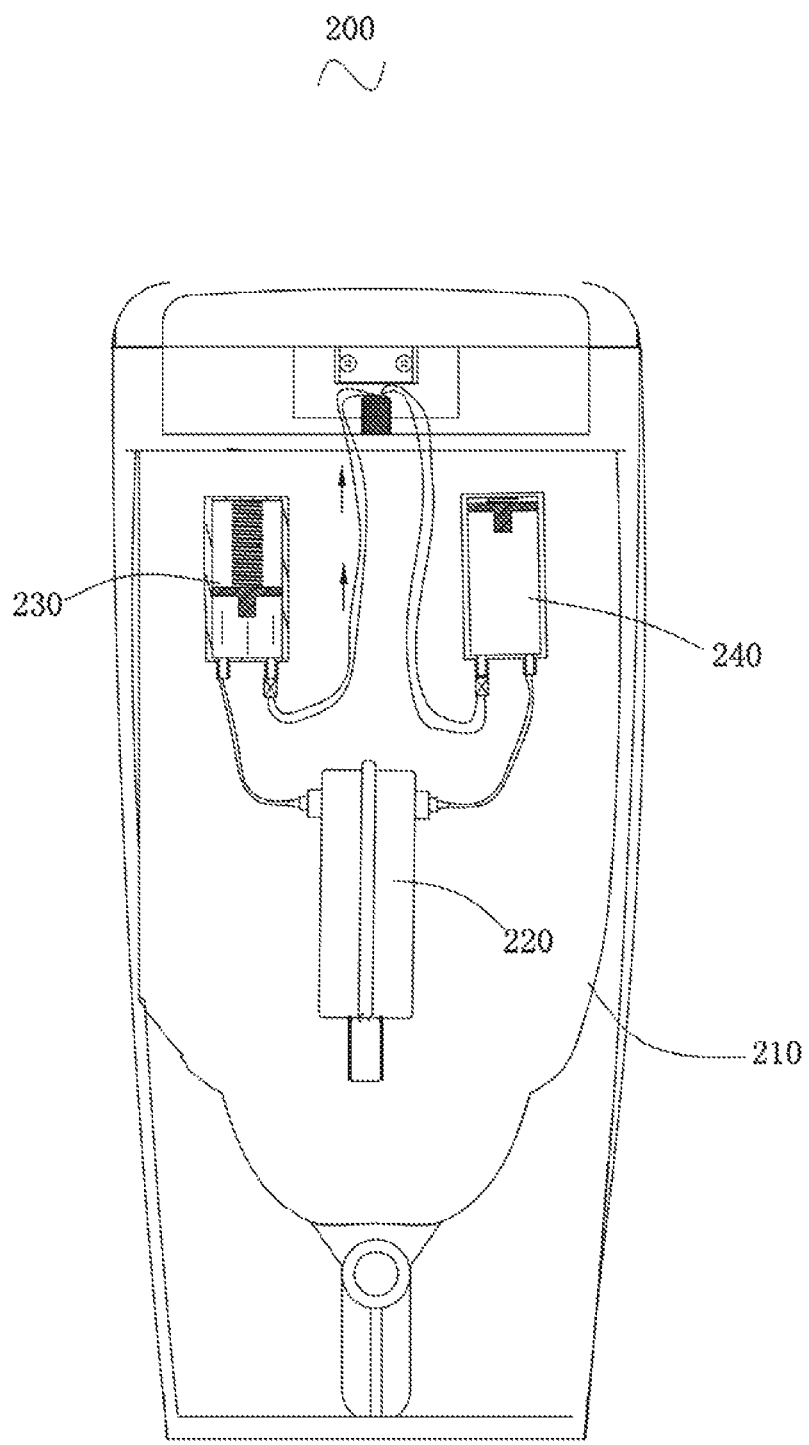
FIG. 6 is the schematic diagram of the water output of the first water storage module in the electrolytic water urinal as shown in FIG. 3.
Figure 7:
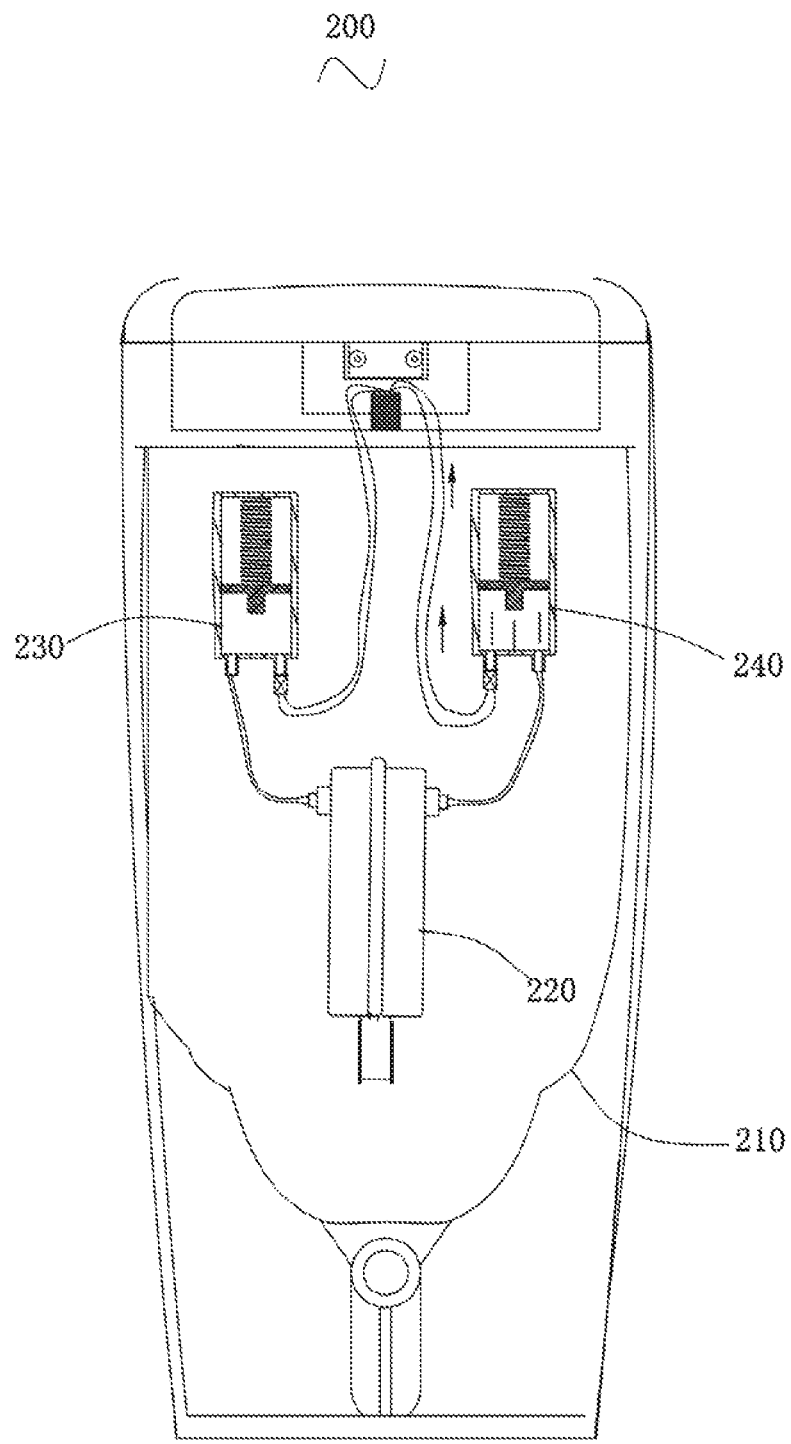
FIG. 7 is the schematic diagram of the water output of the second water storage module in the electrolytic water urinal as shown in FIG. 3.

Referring to FIG. 5, FIG. 6, and FIG. 7, when water is input into the first water storage module 230 or the second water storage module 240, the alkaline electrolytic water or the acidic electrolytic water enters the reservoir body 201 and pushes the push plate 203 to compress the spring 202, so as to achieve the functions of energy storage and water storage of the first water storage module 230 or the second water storage module 240.

When water is discharged from the second water storage module 240 or first water storage module 230, the compressed spring 202 pushes the push plate 203 to move, such that the alkaline electrolytic water or the acidic electrolytic water in the reservoir body 201 is discharged by means of the push plate 203 under a pressure so as to achieve the water discharging.

When the user is using the electrolytic water urinal 200 in a normal mode, the electrolysis module 220 of the electrolytic water urinal 200 does not start, and regular tap water is used to wash the electrolytic water urinal 200 to perform the neutral water washing.

When there is no user using the electrolytic water urinal 200, the electrolytic water urinal 200 would automatically start the electrolysis module 220 to produce the acidic electrolytic water and the alkaline electrolytic water to perform electrolytic water washing on the electrolytic water urinal 200. Further, the electrolytic water urinal 200 selects a predetermined time interval to perform electrolytic water washing operation. For example, the electrolytic water urinal 200 may perform electrolytic water washing operation every 6 hours, 12 hours, 24 hours, etc.

Moreover, before performing the electrolysis through the electrolysis module 220 to produce the acidic electrolytic water and the alkaline electrolytic water, it is required that the water is supplied in the electrolysis module 220 first, and subsequently the power is supplied to start the electrolysis module 220.

The electrolytic water washing process of the electrolytic water urinal 200 includes an acidic washing step and an alkaline washing step that are performed separately.

In the acidic washing step, the electrolysis module 220 in the electrolytic water urinal 200 starts to work, and the first control valve 250 is open, such that the acidic electrolytic water enters the bowl water inlet 211 of the urinal body 210 from the first water storage module 230 and is sprayed evenly on the inner wall of the urinal body 210 through the nozzle, so as to implement the acidic washing operation from top to bottom. During this time, the alkaline electrolytic water remains stored in the second water storage module 240.

After finishing the acidic electrolytic water washing, the alkaline washing step is performed. The first control valve 250 is closed, and the second control valve 260 is open, such that the alkaline electrolytic water enters the bowl water inlet 211 of the urinal body 210 from the second water storage module 240 and is sprayed evenly on the inner wall of the urinal body 210 through the nozzle, so as to implement the alkaline washing operation from top to bottom. Thus, the electrolytic water washing process of the urinal body 210 is performed once.

It should be noted that, when the acidic electrolytic water or the alkaline electrolytic water is discharged from the first water storage module 230 and the second water storage module 240 respectively, since the spring 202 and the push plate 203 work in collaboration, the acidic electrolytic water or the alkaline electrolytic water is sprayed at a certain initial velocity from the nozzle 212, to achieve the purpose of washing.

That is, in the electrolytic water urinal 200 provided by the present embodiment, the acidic electrolytic water and the alkaline electrolytic water produced by the electrolysis module 220 are separate from each other and are sprayed on the inner wall of the urinal body 210 alternately through the water inlet 211 of the bowl urinal body 210, to fulfill the washing operation of the electrolytic water urinal 200.

In other alternative embodiments, in the washing process of the electrolytic water urinal 200, the alkaline washing step may be performed first and the acidic washing step may be performed subsequently. The specific process is similar to the above electrolytic water washing process, and thus the details are omitted here.

Optionally, the electrolytic water urinal 200 may also include an electrolytic water controlling module (not shown) which controls the electrolysis module 220 to switch the electrodes. The electrolytic water controlling module may be hardware, such as a control circuit, a control chip, a programmable single chip, and so on, and may also be software, to which the present invention is not limited.

After the electrodes of the electrolysis module 220 are switched by the electrolytic water controlling module controls, the first water outlet 221 is configured to discharge the alkaline electrolytic water, and the second water outlet 222 is configured to discharge the acidic electrolytic water. Correspondingly, the first water storage module 230 is configured to store alkaline electrolytic water discharged by the first water outlet 221, and the second water storage module 240 is configured to store acidic electrolytic water discharged by the second water outlet 222.

Embodiment 3

Figure 8:
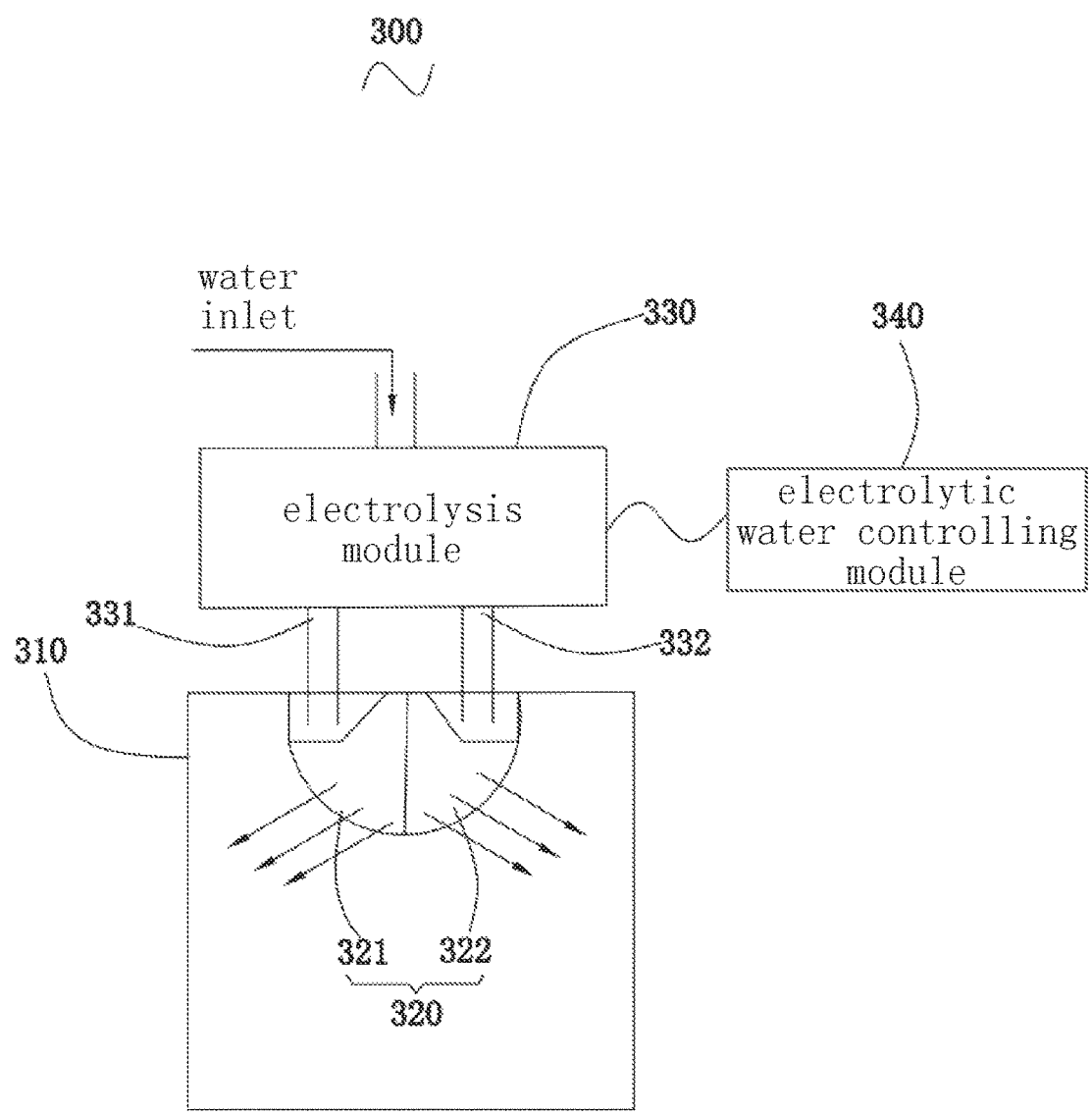
FIG. 8 is the structural schematic diagram of the electrolytic water urinal provided by Embodiment 3 of the present invention.
Figure 9:
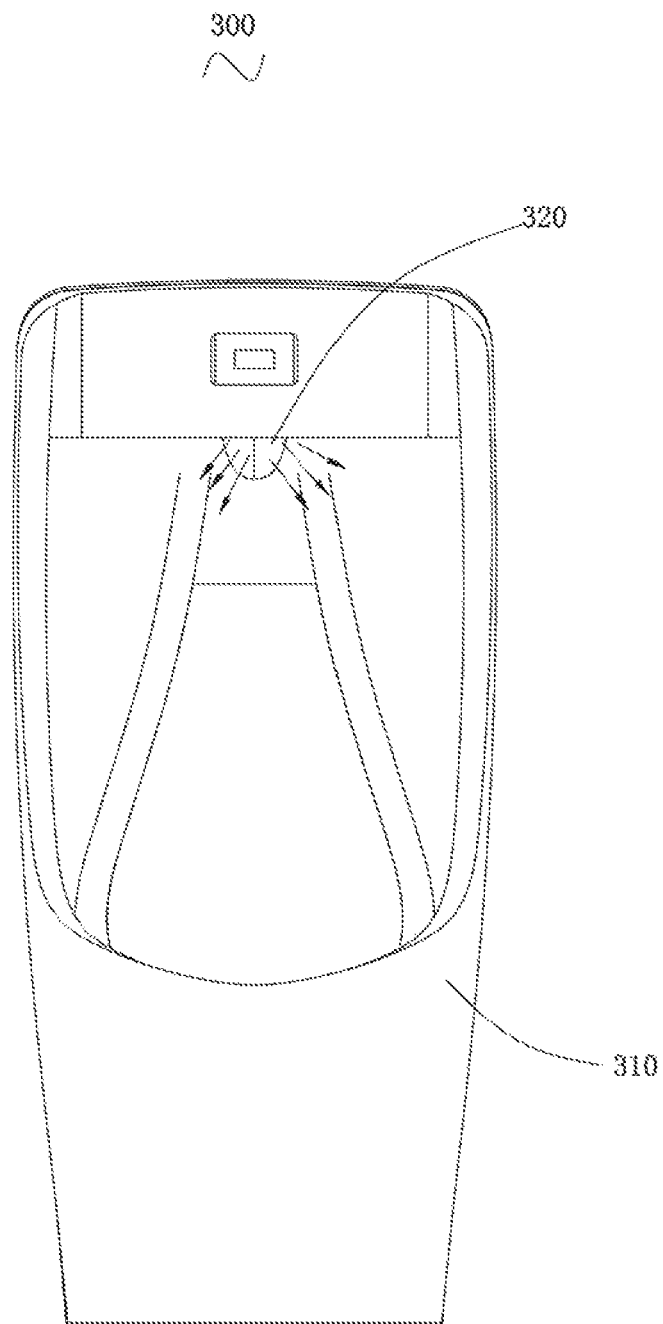
FIG. 9 is the assembling structural schematic diagram of the electrolytic water urinal as shown in FIG. 8.

Referring to both FIG. 8 and FIG. 9, the electrolytic water urinal 300 includes a urinal body 310, a nozzle 320, an electrolysis module 330, and an electrolytic water controlling module 340. In the present embodiment, the electrolytic water controlling module 340 controls the electrolysis module 330 to switch the electrodes. Optionally, the electrolytic water controlling module 340 may be hardware, such as a control circuit, a control chip, a programmable single chip, and so on, and may also be software, to which the present invention is not limited.

The urinal body 310 includes a bowl water inlet (not shown) which is provided on the top of the urinal body 310.

Figure 10:
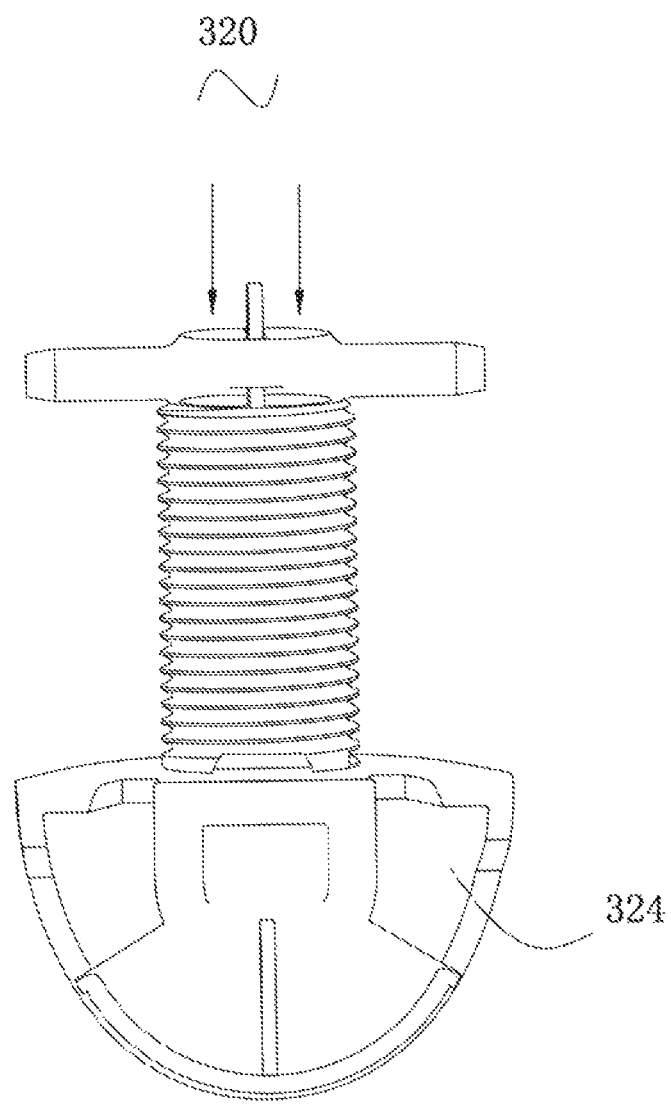
FIG. 10 is the structural schematic diagram of the nozzle in the electrolytic water urinal as shown in FIG. 8.
Figure 11:
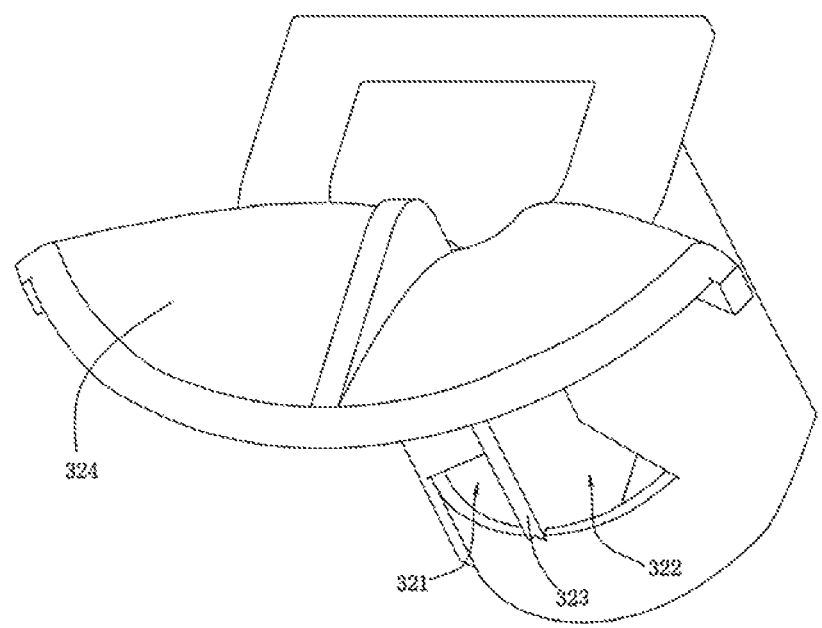
FIG. 11 is the structural schematic diagram of the split blade, the first spout, and the second spout in the nozzle as shown in FIG. 10.

Referring to both FIG. 10 and FIG. 11, the nozzle 320 is provided at the bowl water inlet of the urinal body 310 and is connected to the bowl water inlet. The nozzle 320 includes a first spout 321, a second spout 322, and a split blade 324. The first spout 321 and the second spout 322 are provided adjacently and are spaced by a baffle plate 323. The split blade 324 is provided on the first spout 321 and the second spout 322, and is used to disperse the liquid flowing from the first spout 321 and the second spout 322.

The electrolysis module 330 produces the acidic electrolytic water and the alkaline electrolytic water and includes a first water outlet of 331 and a second water outlet 332.

The first spout 321 of the nozzle 320 is directly connected to the first water outlet 331 of the electrolysis module 330. The second spout 322 is directly connected to the second water outlet 332 of the electrolysis module 330. Thus, the first water outlet 331 and the second water outlet 332 of the electrolysis module 330 are separately connected to the bowl water inlet of the urinal body 310. Accordingly, the washing of both sides of the urinal body 310 is implemented.

When the user is using the electrolytic water urinal 300 in a normal mode, the electrolysis module 330 of the electrolytic water urinal 300 does not start, and regular tap water is used to wash the electrolytic water urinal 300 to perform the neutral water washing.

When there is no user using the electrolytic water urinal 300, the electrolytic water urinal 300 would automatically start the electrolysis module 330 to produce the acidic electrolytic water and the alkaline electrolytic water to perform electrolytic water washing on the electrolytic water urinal 300. Further, the electrolytic water urinal 300 selects a predetermined time interval to perform electrolytic water washing operation once. For example, the electrolytic water urinal 300 may perform the electrolytic water washing operation every 6 hours, 12 hours, 24 hours, etc.

Moreover, before performing the electrolysis through the electrolysis module 330 to produce the acidic electrolytic water and the alkaline electrolytic water, it is required that the water is supplied in the electrolysis module 330 first, and then the power is supplied to start the electrolysis module 330.

The electrolytic water washing process of the electrolytic water urinal 300 includes the first washing process and the second washing process that are performed separately.

In the first washing process of the urinal body 310, the electrolytic water controlling module 340 controls the cathode and the anode of the electrolysis module 330, such that the electrolysis module 330 produces acidic electrolytic water in the corresponding region of the first water outlet 331, and produces alkaline electrolytic water in the corresponding region of the second water outlet 332. Moreover, the acidic electrolytic water and the alkaline electrolytic water produced by the electrolysis module 330 are sprayed simultaneously from the first spout 321 and the second spout 322 of the nozzle 320 respectively to the inner walls of both sides of the urinal body 310, so as to wash the urinal body 310 from top to bottom. Also, the acid-alkaline neutralization reaction occurs at the bottom of the urinal body 310 to produce neutral water, so as to fulfill the washing operation of the urinal body 310.

In the second washing process of the urinal body 310, the electrolytic water controlling module 340 switches the cathode and the anode of the electrolysis module 330, such that the alkaline electrolytic water is produced in the corresponding region of the first water outlet 331, and the acidic electrolytic water is produced in the corresponding region of the second water outlet 332. Moreover, the acidic electrolytic water and the alkaline electrolytic water produced by the electrolysis module 330 are simultaneously sprayed from the second spout 322 and the first spout 321 of the nozzle 320 respectively to the inner wall of the urinal body 310, so as to wash the urinal body 310 from top to bottom. Also, the acid-alkaline neutralization reaction occurs at the bottom of the urinal body 310 to produce neutral water, so as to fulfill the washing operation of the urinal body 310.

Accordingly, the washing operation in which the acidic electrolytic water and the alkaline electrolytic water are exchanged is performed once.

In the electrolytic water urinal 300 provided by the present embodiment, since the acidic electrolytic water and the alkaline electrolytic water are exchanged to wash the urinal body 310, the corrosion to the nozzle 320 caused by the ever-lasting acidic or alkaline environment is avoided. The lifetime of the apparatus is prolonged. Residual urine scales on the inner wall of the urinal body 310 can be removed completely. The functions of sterilization and disinfection are achieved.

Of course, the present invention is not limited to the present embodiment. In other alternative embodiments, in the washing process of the electrolytic water urinal 300, the electrolytic water urinal 300 may also perform the second washing process first and perform the first washing process subsequently, such that the washing operation in which the acidic electrolytic water and the alkaline electrolytic water are exchanged is performed once. The specific process is similar to the above electrolytic water washing process, and thus the details are omitted here.

Embodiment 4

Figure 12:
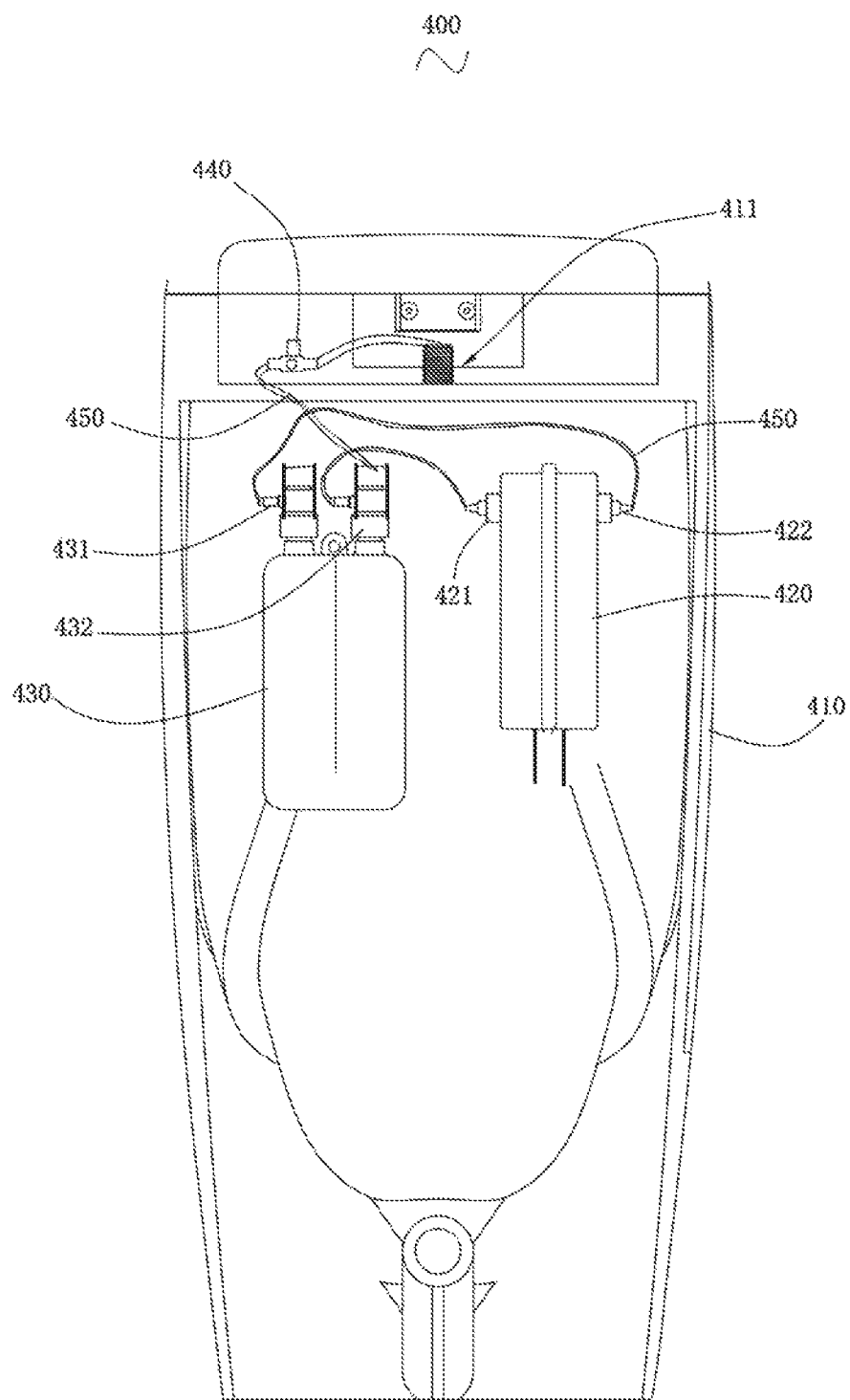
FIG. 12 is the structural schematic diagram of the electrolytic water urinal provided by Embodiment 4 of the present invention.

Referring to FIG. 12, it is the structural schematic diagram of the electrolytic water urinal provided by Embodiment 4 of the present invention. The electrolytic water urinal 400 includes a urinal body 410, an electrolysis module 420, a water storage module 430, a control valve 440, and tubes 450. Preferably, the control valve 440 is a solenoid valve. Optionally, tubes 450 may be plastic tubes or tubes made of metal, to which the present invention is not limited.

The urinal body 410 includes a bowl water inlet 411, which is provided on the upper portion of the urinal body. Further, the urinal body 410 is also provided with a nozzle (not shown) which is connected to the bowl water inlet 411. The nozzle is provided on the inner side of the top of the urinal body 410 and has an opening oriented to the inside of the urinal body 410.

The electrolysis module 420 produces the acidic electrolytic water and the alkaline electrolytic water and includes a first water outlet 421 which is configured to discharge the acidic electrolytic water and a second water outlet 422 which is configured to discharge the alkaline electrolytic water.

The water storage module 430 includes a water inlet 431 and a water outlet 432 that are both provided on the top of the water storage module 430.

In the present embodiment, the e water inlet 431 of the water storage module 430 is connected to the second water outlet 422 of the electrolysis module 420 through the tube 450. The water outlet 432 of the water storage module 430 and the first water outlet 421 of the electrolysis module 420 are connected to each other and jointly connected to the control valve 440 and the bowl water inlet 411 of the urinal body 410 in turn through the tube 450.

Moreover, the serpentine channels are formed inside the water storage module 430. That is, the water inlet 431 of the water storage module 430 is connected to the water outlet 432 of the water storage module 430 through the serpentine channels. In the present embodiment, the water storage module 430 is provided with at least one baffle plate (not shown). The baffle plate separates the water storage space in the water storage module 430 into serpentine channels that are connected to each other.

During the water input, in order to ensure that the air in the serpentine channels of the water storage module 430 is totally evacuated, both the water inlet 431 of the water storage module 430 and the serpentine channels are provided horizontally. That is, when the acidic electrolytic water or the alkaline electrolytic water enters the water storage module 430, the acidic electrolytic water or the alkaline electrolytic water horizontally enters the water inlet 431 of the water storage module 430, and gradually flows to the water outlet 432 of the water storage module 430, from bottom to top through the serpentine channels which are horizontally provided, so as to evacuate the air in the serpentine channels of the water storage module 430.

When the electrolytic water urinal 400 is used normally, the control valve 440 is open, but the electrolysis module 420 does not start up. Thus, cleaning water directly flows through the electrolysis module 420 and directly flows into the urinal body 410 to perform the neutral water washing on the urinal body 410.

When the electrolytic water urinal body 400 is performing the electrolytic water washing, the washing process of the electrolytic water urinal 400 includes an acidic washing step, an alkaline washing step, and the neutral water washing step that are performed sequentially.

It should be noted that only when there is no user using the urinal, would the electrolytic water urinal body 400 start the electrolysis module 420 to perform the electrolytic water washing. Further, the electrolytic water urinal 400 selects a predetermined time interval to perform electrolytic water washing operation once. For example, the electrolytic water urinal 400 may perform the electrolytic water washing operation every 6 hours, 12 hours, 24 hours, etc.

Moreover, before performing the electrolysis through the electrolysis module 420 to produce the acidic electrolytic water and the alkaline electrolytic water, it is required that the water is supplied in the electrolysis module 420 first, and then the power is supplied to start the electrolysis module 420.

In the acidic washing step, the control valve 440 is open and the electrolysis module 420 starts up. The electrolysis module 420 correspondingly produces the equal amounts of the acidic electrolytic water and the alkaline electrolytic water. The acidic electrolytic water directly enters the bowl water inlet 411 of the urinal body 410 through the tube 450 and is sprayed into the urinal body 410 through the nozzle, so as to wash the inner wall of the urinal body 410 from top to bottom to finish the acidic washing step. During this time, the alkaline electrolytic water is stored in the water storage module 430 through the water inlet 431 of the water storage module 430.

When a certain amount of the alkaline electrolytic water is stored in the water storage module 430, the power is cut off to stop the electrolysis operation of the electrolysis module 420. The alkaline washing step is then performed.

In the alkaline washing step, neutral cleaning water is introduced into the electrolysis module 420. The cleaning water enters the water storage module 430 from the water inlet 431 of the water storage module 430 to force the alkaline electrolytic water in the water storage module 430 to enter the bowl water inlet 411 of the urinal body 410 from the water outlet 432 of the water storage module 430. The alkaline electrolytic water is sprayed into the urinal body 410 through the nozzle, so as to wash the inner wall of the urinal body 410 from top to bottom to fulfill the alkaline washing step.

After finishing the discharging of the alkaline electrolytic water, the neutral water washing step is performed.

In the neutral water washing step, the clean water from the water outlet 432 of the water storage module 430 enters the bowl water inlet 411 of the urinal body 410 and is sprayed into the urinal body 410 through the nozzle to wash the inner wall of the urinal body 410 from top to bottom, so as to fulfill the neutral water washing step.

Accordingly, the washing operation of the electrolytic water urinal 400 is performed once.

In other alternative embodiments, in the washing process of the electrolytic water urinal 400, the electrolytic water urinal 400 may first perform the alkaline washing step, then the acidic washing step, and finally the neutral water washing step, such that the washing operation in which the acidic electrolytic water and the alkaline electrolytic water are exchanged is performed once. When the alkaline washing step is performed, the acidic electrolytic water is stored in the water storage module 430.

Optionally, the electrolytic water urinal 400 may also include an electrolytic water controlling module (not shown) which controls the electrolysis module 420 to switch the electrodes. The electrolytic water controlling module may be hardware such as a control circuit, a control chip, a programmable single chip, and so on, and may also be software, to which the present invention is not limited.

After the electrodes of the electrolysis module 420 are switched by the electrolytic water controlling module, the first water outlet 421 of the electrolysis module 420 is configured to discharge the alkaline electrolytic water, and the second water outlet 422 of the electrolysis module 420 is configured to discharge the acidic electrolytic water. Correspondingly, the alkaline electrolytic water discharged by the first water outlet 421 of the electrolysis module 420 directly flows into the urinal body 410, while the water storage module 430 is configured to store acidic electrolytic water discharged by the second water outlet 422 of the electrolysis module 420.

Compared to the prior art, beneficial effects of the electrolytic water urinal provided by the present invention include:

1. In the electrolytic water urinal, the acidic electrolytic water and the alkaline electrolytic water produced by the electrolysis module are used to separately wash the urinal body, and converge at the bottom of the urinal body to lead to the neutralization reaction so as to produce neutral water. In the washing process, the acidic electrolytic water may directly and chemically react with the urine scale. The functions of sterilization and disinfection are maintained. Thus, the functions of sterilization, disinfection, deodorization, and urine scale removal from the electrolytic water urinal can be improved. Moreover, since the acidic electrolytic water and the alkaline electrolytic water are used together to perform the washing, the purpose of saving water can also be achieved.

2. In the electrolytic water urinal, the acidic electrolytic water and the alkaline electrolytic water are used to wash the urinal body alternately. The neutralization reaction occurs at the bottom of the urinal body to produce neutral water. Thus, the following problem is avoided, i.e., when the acidic electrolytic water and the alkaline electrolytic water are output at the same time, they contact each other which leads to the neutralization reaction and thereby losing the functions of sterilization and disinfection. Thus, the functions of sterilization, disinfection, deodorization, and urine scale removal from the electrolytic water urinal are improved.

3. In the electrolytic water urinal, each of the second water storage module and the first water storage module is provided with a spring. The functions of energy storage and water storage are achieved through the extension and retraction of the spring. Moreover, the acidic electrolytic water and the alkaline electrolytic water can be discharged under a pressure, such that a jet washing flow with a certain flow rate is sprayed on the inner wall of the urinal body. Not only is the washing effect excellent, but also the water saving function is achieved. Moreover, since the acidic electrolytic water and the alkaline electrolytic water alternately wash the urinal body, the following problem can be avoided, i.e., when the acidic electrolytic water and the alkaline electrolytic water are output at the same time, they contact each other which leads to the neutralization reaction, and thereby losing the functions of sterilization and disinfection. Thus, the functions of sterilization, disinfection, deodorization, and urine scale removal from the electrolytic water urinal are improved.

4. In the electrolytic water urinal, the first spout and the second spout of the nozzle are used to make the acidic electrolytic water and the alkaline electrolytic water respectively wash the inner walls of both sides of the urinal body. Moreover, the problem that the acidic electrolytic water and the alkaline electrolytic water contact each other, which leads to the neutralization reaction and thereby losing the function of sterilization and disinfection, is avoided. Thus, the functions of sterilization, disinfection, deodorization, and urine scale removal from the electrolytic water urinal are improved. Also, the electrolytic water controlling module controls the electrolysis module to switch the cathode and the anode, such that the washing operations in which the acidic electrolytic water and the alkaline electrolytic water are exchanged are achieved. Not only can lifetimes of electrodes of the electrolytic cell be improved, but also the urinal can be washed better.

5. In the electrolytic water urinal, the washing process of the electrolytic water urinal includes an acidic washing step, an alkaline washing step, and a neutral water washing step that are performed separately and sequentially. Thus, the acidic electrolytic water and the alkaline electrolytic water alternately wash the urinal body. Also, at the bottom of the urinal body, the neutralization reaction occurs to produce neutral water. Thus, the following problem can be avoided, i.e., when the acidic electrolytic water and the alkaline electrolytic water are output at the same time, they contact each other, which leads to the neutralization reaction, and thereby losing the functions of sterilization and disinfection. Thus, the functions of sterilization, disinfection, deodorization, and urine scale removal from the electrolytic water urinal are improved.

The above description illustrates and depicts preferred embodiments of the present invention. As described above, it should be construed that the present invention is not limited to the embodiments disclosed here, and other embodiments should not be excluded. Rather, the present invention can be used in various combinations, modifications, and environments. Moreover, within the scope of the inventive concept herein, the present invention can be altered in light of the above teachings, technologies or knowledge in the related art. However, the modifications and variations made by a person of ordinary skill in the art, without departing from the spirit and scope of the present invention, should all fall within the scope of the appending claims of the present invention.

What is claimed is:

1. An electrolytic water urinal, comprising:
   an electrolysis module producing acidic electrolytic water and alkaline electrolytic water and including a first water outlet and a second water outlet; and
   a urinal body including a bowl water inlet provided on an upper portion of the urinal body;
   wherein
   the first water outlet and the second water outlet of the electrolysis module are configured to alternately discharge the acidic electrolytic water and the alkaline electrolytic water and separately connected to the bowl water inlet of the urinal body; and
   the acidic electrolytic water and the alkaline electrolytic water produced by the electrolysis module are alternately or separately sprayed on an inner wall of the urinal body through the bowl water inlet to perform washing from top to bottom.

2. The electrolytic water urinal of claim 1, further comprising
   a water storage module including a first reservoir and a second reservoir isolated from each other;
   a first control valve;
   a second control valve; and
   a tube;
   wherein
   a water inlet of the first reservoir is connected to the first water outlet of the electrolysis module through the tube;
   a water outlet of the first reservoir, the first control valve, and the bowl water inlet of the urinal body are connected in turn through the tube;
   a water inlet of the second reservoir is connected to the second water outlet of the electrolysis module through the tube;
   a water outlet of the second reservoir, the second control valve, and the bowl water inlet of the urinal body are connected in turn through the tube; and
   the acidic electrolytic water and the alkaline electrolytic water are alternately sprayed on the inner wall of the urinal body through the bowl water inlet.

3. The electrolytic water urinal of claim 2, wherein
   the acidic electrolytic water washes the inner wall of the urinal body from top to bottom first, and the alkaline electrolytic water starts to wash the inner wall of the urinal body from top to bottom subsequently;
   or
   the alkaline electrolytic water washes the inner wall of the urinal body from top to bottom first, and the acidic electrolytic water starts to wash the inner wall of the urinal body from top to bottom subsequently.

4. The electrolytic water urinal of claim 1, further comprising
   a first water storage module;
   a second water storage module;
   a first control valve;
   a second control valve; and
   a tube;
   wherein
   a water inlet of the first water storage module is connected to the first water outlet of the electrolysis module through the tube;
   a first water outlet of the first water storage module, the first control valve, and the bowl water inlet of the urinal body are connected in turn through the tube;
   a water inlet of the second water storage module is connected to the second water outlet of the electrolysis module through the tube;
   a second water outlet of the second water storage module, the second control valve, and the bowl water inlet of the urinal body are connected in turn through the tube; and
   the acidic electrolytic water and the alkaline electrolytic water are alternately sprayed on the inner wall of the urinal body through the bowl water inlet.

5. The electrolytic water urinal of claim 4, wherein
   each of the first water storage module and the second water storage module includes a reservoir body provided with a water inlet and a water outlet, a spring, and a push plate;
   the spring and the push plate are both provided in the reservoir body;
   the spring is fixed between the push plate and an inner wall of the reservoir body and is provided far away from the water inlet of the reservoir body and the water outlet of the reservoir body;
   when water is filled into the second water storage module or the first water storage module, the alkaline electrolytic water or the acidic electrolytic water enters the reservoir body and pushes the push plate to compress the spring so as to achieve a water storage; and
   when the water is discharged from the second water storage module or the first water storage module, a compressed spring pushes the push plate to move, such that the alkaline electrolytic water or the acidic electrolytic water in the reservoir body is discharged by means of the push plate under a pressure so as to achieve water discharging.

6. The electrolytic water urinal of claim 1, further comprising
   a water storage module including a water inlet and a water outlet that are both provided on top of the water storage module;

a control valve; and a tube;

wherein the water inlet of the water storage module is connected to the second water outlet of the electrolysis module through the tube;

the water outlet of the water storage module and the first water outlet of the electrolysis module are connected to each other and jointly connected to the control valve and the bowl water inlet of the urinal body in turn through the tube.

7. The electrolytic water urinal of claim 6, wherein the water storage module is provided with at least one baffle plate; and the baffle plate separates a water storage space in the water storage module into a plurality of serpentine channels that are connected to each other.

8. The electrolytic water urinal of claim 7, wherein when the acidic electrolytic water or the alkaline electrolytic water enters the water storage module, the acidic electrolytic water or the alkaline electrolytic water horizontally enters the water inlet of the water storage module, and gradually flows to the water outlet of the water storage module from bottom to top through the plurality of serpentine channels provided horizontally, so as to evacuate air in the serpentine channels of the water storage module.

9. The electrolytic water urinal of claim 6, wherein the acidic electrolytic water directly washes the inner wall of the urinal body from top to bottom and the alkaline electrolytic water is stored in the water storage module;

when a certain amount of the alkaline electrolytic water is stored, the electrolysis module stops an electrolysis operation, and neutral cleaning water is introduced through the water inlet of the water storage module;

the neutral cleaning water enters the water storage module to force the alkaline electrolytic water in the water storage module to enter the urinal body, so as to wash the inner wall of the urinal body from top to bottom; and after discharging of the alkaline electrolytic water is finished, the neutral cleaning water enters the urinal body, so as to wash the inner wall of the urinal body from top to bottom;

or the alkaline electrolytic water directly washes the inner wall of the urinal body from top to bottom and the acidic electrolytic water is stored in the water storage module;

when a certain amount of the acidic electrolytic water is stored, the electrolysis module stops an electrolysis operation, and neutral cleaning water is introduced through the water inlet of the water storage module;

the neutral cleaning water enters the water storage module to force the acidic electrolytic water in the water storage module to enter the urinal body, so as to wash the inner wall of the urinal body from top to bottom; and after discharging of the acidic electrolytic water is finished, the neutral cleaning water enters the urinal body, so as to wash the inner wall of the urinal body from top to bottom.

10. The electrolytic water urinal of claim 1, further comprising an electrolytic water control module controlling the electrolysis module to switch electrodes; and a nozzle provided at the bowl water inlet of the urinal body and including a first spout, a second spout, and a baffle plate provided between the first spout and the second spout;

wherein the first spout and the second spout are provided adjacently and are spaced by the baffle plate;

the first spout is connected to the first water outlet of the electrolysis module directly; and the second spout is connected to the second water outlet of the electrolysis module directly.

11. The electrolytic water urinal of claim 10, wherein the acidic electrolytic water and the alkaline electrolytic water are sprayed simultaneously on inner walls of both sides of the urinal body from the first spout and the second spout of the nozzle respectively.

12. The electrolytic water urinal of claim 1, further comprising an electrolytic water control module controlling the electrolysis module to switch electrodes;

wherein after the electrodes of the electrolysis module is switched through the electrolytic water control module, in the electrolysis module, the first water outlet is configured to discharge the alkaline electrolytic water, and the second water outlet is configured to discharge the acidic electrolytic water.

* * * * *